United States Patent [19]

Löfflmann

[11] Patent Number: 5,516,754

[45] Date of Patent: May 14, 1996

[54] METHOD FOR THE SELECTIVE DISSOLUTION OF CANCER CELLS USING A COMPOSITION DERIVED FROM THE PHOTOSYNTHETIC SYSTEM OF PLANTS AND MAMMALIAN EMBRYONIC TISSUE

[76] Inventor: Adolf Löfflmann, Münchner Strasse 7, 8000 Munich 70, Germany

[21] Appl. No.: 168,324

[22] Filed: Jan. 24, 1994

Related U.S. Application Data

[63] Continuation of Ser. No. 613,503, filed as PCT/EP90/00388, Mar. 9, 1990, abandoned.

[30] Foreign Application Priority Data

Mar. 10, 1989 [DE] Germany ............... 39 07 822.1

[51] Int. Cl.⁶ .................... A61K 38/44; A61K 38/17; A61K 38/56
[52] U.S. Cl. ................. 514/2; 514/21; 424/94.1; 424/94.4; 530/370; 530/379; 530/850; 530/851
[58] Field of Search ............ 514/2, 21; 424/94.1, 424/94.4; 530/370, 379, 850, 851

[56] References Cited

U.S. PATENT DOCUMENTS

| | | | |
|---|---|---|---|
| 4,335,040 | 6/1982 | Livingston | 530/851 |
| 4,496,539 | 1/1985 | Plotkin et al. | 424/94.4 |
| 4,708,948 | 11/1987 | Iwata et al. | 424/85.1 |

FOREIGN PATENT DOCUMENTS 0079200  3/1989  Japan.

*Primary Examiner*—Stephen G. Walsh
*Attorney, Agent, or Firm*—Henry M. Feiereisen

[57] ABSTRACT

By the combined use of an agent which selectively dissolves tumor cells and which contains a protein fraction which has oxygen-liberating action and which is derived from the photosynthetic system of plants, together with a further agent which inhibits the proteases of the cancer cells and which has been obtained by means of extraction of embryonic tissue or maternal uterus tissue from placentals, it is possible to selectively dissolve the tumor by means of this agent without damaging the healthy organism. When used on its own, the abovementioned plant-derived agent shows an activity in the treatment of inflammatory processes and is also suitable for the aftertreatment of scars, keloids and damage caused by ionizing rays.

9 Claims, 1 Drawing Sheet

METHOD FOR THE SELECTIVE DISSOLUTION OF CANCER CELLS USING A COMPOSITION DERIVED FROM THE PHOTOSYNTHETIC SYSTEM OF PLANTS AND MAMMALIAN EMBRYONIC TISSUE

This is a continuation of application Ser. No. 07/613,503, filed as PCT/EP90/00388, Mar. 9, 1990, now abandoned, and constituting the national phase of PCT/EP90/00388, designating the U.S.

The invention relates to the use of certain substances which are illustrated below in greater detail, based on a novel concept in medical science, as an active substance in pharmaceuticals, in particular for the selective dissolution (destruction) of cancer cells (malign tumor cells), but also for combating inflammatory processes, and for the treatment of hypertrophic scars and keloids.

The present invention is based on considerations that one of the reasons why scientific attempts to date to understand and combat cancer may have remained so unsatisfactory is because the underlying idea that the phenomenon of cancer is causally linked to the cell nucleus has blurred focusing on fundamentally novel, promising concepts. Cancer cells differ from healthy cells by a series of properties, and successful cancer therapy should, if possible, be orientated towards these properties which distinguish cancer cells from healthy cells so as to be able to choose a therapy route which selectively only targets cancer cells, or selectively only damages cancer cells. However, numerous known methods in cancer therapy do not meet these requirements since, like most cytostatic agents and rays, for example, they do not selectively act on cancer tissue, but also damage normal healthy tissue. A method for destroying tumors, which is known from the literature, is described in Nachr. Chem. Tech. Lab. 33 (1985), No. 7 "Lokalisierung und Therapie von Tumoren mit Porphyrinen [Tumor localization therapy with porphyrins]", H. Vandenbergh and P. Cornaz. This method combines injections with a haematoporphyrin derivative with red-light irradiation.

The present invention is based on the known observation that cancer cells differ from healthy cells in that they have an "anoxemic metabolism" which is characterized by the occurrence of aerobic glycolysis. Starting from this medical fact, the consideration was that therapy which, in a targeted manner, aims at the cell respiration of cancer cells, which differs from that of healthy cells, can selectively damage the former without simultaneously attacking healthy cells. However, when this concept was pursued, it emerged that further peculiarities of cancer cells compared with normal cells have to be taken into account if therapy is to be successful, and that valuable model hypotheses can be put forth if the cancer cell is regarded as a cell which, in total, mimics embryonic behavior (embryonic encoding). However, the properties exhibited by cancer cells similar to embryonic cells, include not only the anoxemic cell metabolism, but also the fact that proteases are active, which imparts the ability of "incipient digestion" of body tissue (maternal uterus tissue or healthy tissue of the cancer patient) to the cancer cells and to the embryonic cells.

Based on these trains of thought, a novel cancer therapy has been developed whose effectiveness has been confirmed in animal experiments and which has already proved clinically successful in individual cases. This novel cancer therapy consists in a method of selectively dissolving cancer cells in live organisms of warm-blooded species by administering in combination, namely either one shortly after the other or in the form of a mixture, by way of injection or infusion, a protein fraction with oxygen activity from the photosynthetic system of plants or precursors thereof and a protein mixture of embryonic tissue or maternal uterus tissue of placentals, administration being carried out in the form of sterile, isotonic and endotoxin-free solutions.

The fact that certain plant extracts have an effect which inhibits the growth of cancer cells has already been described in various publications (cf., for example, Planta Med. 1985, (6), 538–539; German Auslegeschrift 1,617, 391). However, these publications deal with effects which can be described as bringing under control tumor growth and retarding it, but not tumor dissolution. German Offenlegungsschrift 2,920,631 claims the use of a pressed sap of insectivorous plants, in particular Venus fly-trap, and it claims dissolution of tumors. However, the success of the above described treatment is disputed, and the use of the abovementioned pressed sap is unacceptable because of a high endotoxin content.

It is furthermore known that placenta extracts, in particular bovine placenta, can have a tumor-specific inhibition effect (Exp. Path., Vol. 8, page 205–212, and also Vol. 9, page 354–360; Österreichische Zeitschrift für Onkologie, 1974, Number 2, page 31–37, and also loc. cit., 1977, Number 2–3, page 42–46; EP-A-136,093). Such extracts are described as inhibiting the growth of tumor cells, but nothing is reported about in-vivo dissolution of cancer tumors.

The combination of using plant extracts together with an extract fraction obtained from embryonic tissue has hitherto not been described. The possibility that a tumor can be dissolved using an active substance combination of the abovementioned type can therefore, of course, likewise not be seen from the prior art. In developing the present invention it emerged that a combination of two protein fractions, or protein mixtures, of different origin, which will be described in greater detail in what follows, are selectively effective in the sense of a dissolution of tumor cells, while no comparable effect is obtained when one of the two abovementioned fractions is administered on its own.

The patent claims of the present application are intended to cover the aspects, accessible to patent law, of the novel cancer therapy which is disclosed with the present application and which represents a solution for the task of providing therapy which makes possible selective dissolution of cancer cells using medicaments which are entirely harmless for the healthy body and healthy cells.

The invention therefore relates, on the one hand, to a protein fraction which has oxygen activity and which is derived from the photosynthetic system of plants or from its precursors, for use as a pharmaceutical active substance to be administered by way of injection or infusion, in combination with a protein mixture derived from embryonic tissue or from maternal uterus tissue of placentals, for the selective dissolution of cancer cells in live organisms of warm-blooded species.

The invention furthermore also relates to such a protein fraction for use in the aftertreatment of scars, keloids and inflammatory processes caused by the action of ionizing rays.

The invention furthermore relates to pharmaceutical preparations containing (a) a protein fraction which has oxygen activity and which is derived from the photosynthetic system of plants or from its precursors, and (b) a protein mixture derived from embryonic tissue or maternal uterus tissue of placentals, as a preparation combination to be administered by way of injection or infusion, as a mixture or in immediate succession, for the selective dissolution of cancer cells in live organisms of warm-blooded species.

The invention therefore relates, on the one hand, to the use of a substance class which has, to the knowledge of the applicant, hitherto not been used as a pharmaceutical, namely to the use of protein fractions which have oxygen activity (liberation of oxygen from water under the influence of light and/or heat) from the photosynthetic system of fresh or, if appropriate, dried plants or lower autotrophic organisms, as the active substance of a pharmaceutical which can be administered by way of injection or infusion in combination with a protein mixture derived from embryonic cells or maternal uterus tissue, for the selective dissolution (destruction) of cancer cells.

The reason why a protein fraction from the photosynthetic system of autotrophic plants or autotrophic lower organisms is used is, to put it simply, that during photosynthesis of the plant a series of redox and electron transport processes proceed in the opposite direction than during cell respiration. In higher organisms, the latter takes place in the mitochondria. The electron transfer steps between certain enzymes of the respiratory chain, which are characteristic of cell respiration, are described in detail in textbooks and in the relevant literature. In a cell which operates an anoxemic metabolism, such as a cancer cell, the mitochondria are largely blocked. This can probably be attributed to the fact that electron-donating foreign substances reductively saturate an enzyme of the respiratory chain ($Fe^{3+} \rightarrow Fe^{2+}$) and hence block it for electron uptake from the respiratory chain. By supplying such a blocked cell which operates an anoxemic metabolism (a cancer cell) with a substance which reverses the effect of blocking by an excess electron, the metabolism of such a cell can be caused to collapse, the consequence being cell death. The enzymes of the photosynthetic system of autotrophic plants were recognized as being a substance class which is effective in the above sense. These substances are located in the chloroplasts of green plants, in particular in the thylacoid membrane of these chloroplasts.

The text below describes in greater detail how such a suitable protein fraction is obtained from the photosynthetic system of plants and how it is processed in a suitable manner. It emerged that the effective protein fraction constitutes, or contains, an enzyme which liberates oxygen from $H_2O$ at room temperature (=which has oxygen activity). The isolation and characterization of such protein fractions has also already been described in the literature in some individual cases. Reference is made to Carlsberg Res. Commun. Vol. 45, page 167–176, 1980; Carlsberg Res. Commun. Vol. 46, page 227–242, 1981; Proc. Natl. Acad. Sci. USA, Vol. 77, No. 2, page 957–959, 1980. It is assumed that the protein fraction which is obtained in the manner described below and used in the frame of the present invention, corresponds to the proteins described in the abovementioned publications as regards its effect and, if appropriate, also its nature. It must be mentioned at this point that, irrespective of the fact that the experimental findings were obtained using a protein fraction which had been obtained from a certain plant (*Equisetum arvense*=field horsetail or colt's tail) in a specifically described manner, this specific process and even the specific initial plant material do not seem to be crucial, but it should be possible to isolate a material which is effective in the same sense from most, or all, green plants, since its role in the photosynthetic system of plants is important but not its origin from a particular plant.

However, when an attempt was made to use only the protein fraction from the photosynthetic system of autotrophic plants, it emerged that this was physiologically active when administered by way of injection (intravenously, intramuscularly, subcutaneously), but did not damage cancer cells in the desired sense. It emerged that when the abovementioned substance was injected, a normal tissue showed responses which can be described as anti-inflammatory in the broad sense. Thus, a pronounced effect was observed when the injection was administered after irradiation treatment, by rapidly causing the inflammation in the radiation-damaged normal tissue to subside.

The insignificant effect on cancer cells could then be explained by the fact that the cancer cells prevented the penetration of the protein-type plant enzyme because of increased protease activity (for example collagenase IV), probably resulting in the destruction of the enzyme. By successfully applying the model hypothesis "cancer cell= embryonically encoded cell", it was however possible to overcome this problem by injecting, together with the abovementioned protein fraction from chloroplasts, an extract of embryonic and fetal tissue of placentals, the use of which fraction, in combination with the above-described protein fraction from the photosynthetic system of plants, constitutes an essential element of the present invention. It must be mentioned at this point that the term "placentals" is to be understood in the broadest sense, and that it should also be possible to obtain the active substances required from such tissue of human origin. It is assumed that the effect of additionally injecting the protein mixture extracted from embryonic tissue consists in saturating, blocking or otherwise deactivating the proteases of the cancer cells, so that it is now possible for the proteins from the photosynthetic system of the plants to reach the cancer cell, where they can produce their effects.

This explanation of how injecting embryonic tissue extract works means simultaneously that this extract can advantageously be used in all those cases in which an attempt is made to influence cancer cells with the aid of protein-type plant materials in which, however, the results which are expected on the basis of in-vitro experiments cannot be verified in clinical practice, or only with insufficient clarity.

In what follows, the novel cancer therapy according to the invention will be explained in greater detail by the detailed description of the preparation of the materials used, the results of the animal experiments, and the clinical findings.

It must be mentioned at this point that the preparation processes described do in fact describe one route of obtaining active substances which can be used, but that such substances, or substances which are equally valuable in the sense of the concept of the present invention, also seem to be obtainable by more or less modified similar processes.

Figure 1:
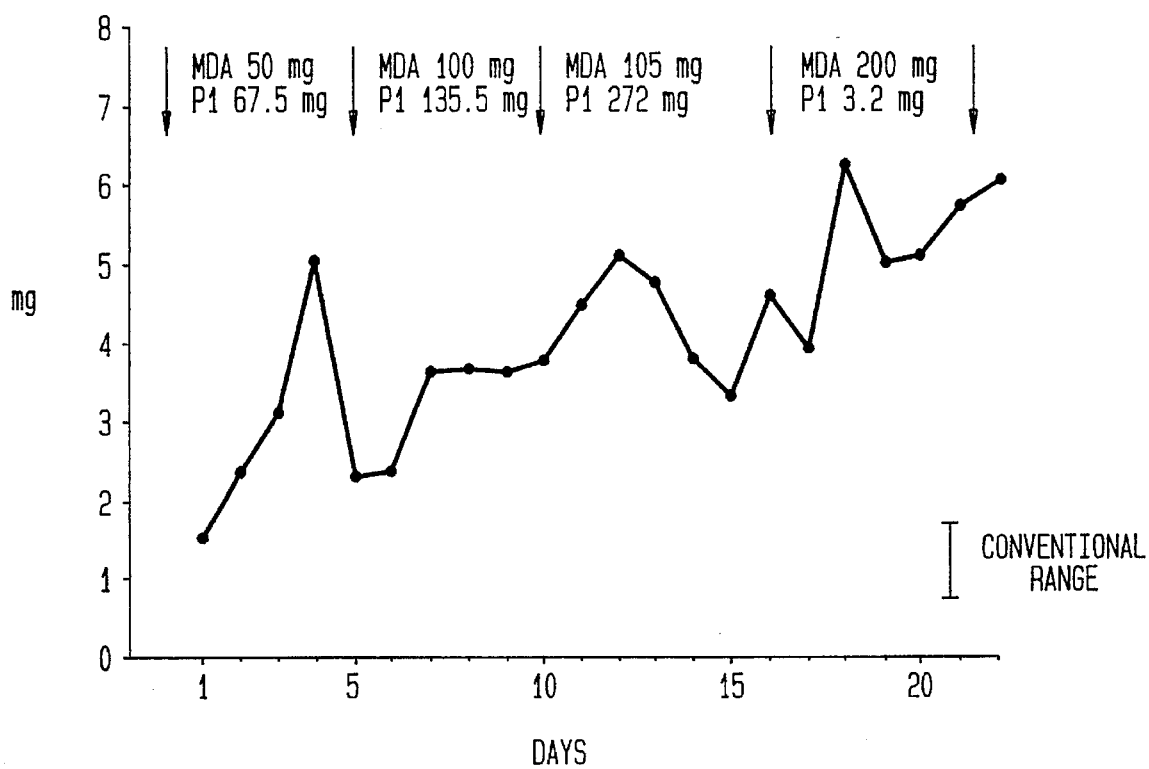
FIG. 1 shows uric acid excretion from a rat treated as in Example III.

I. Preparation and characterization of an oxygen-releasing protein fraction from *Equisetum arvense* chloroplasts.

Starting with fresh stalks and leaves of *Equisetum arvense* (100 g), intact chloroplasts are isolated using a standard procedure as is described, for example, in the book "Praktikum zur Stoffwechselphysiologie der Pflanzen [Practical Course on the Metabolic Physiology of Plants]", Georg Thieme Verlag Stuttgart, New York, 1983, 2nd Edition, pages 66–68. For this purpose, the precomminuted plant material is comminuted in a mixer in the presence of a solution which had been prepared with 0.33M sucrose, 0.01M sodium diphosphate and 5 mM of $MgCl_2$ in a liter of distilled water, with the pH being adjusted to 3 using hydrochloric acid. The resulting homogenized material was pressed and the sap was centrifuged to obtain a chloroplast fraction. The supernatant was discarded, and the chloroplast fraction was washed with a suitable acid isotonic solution (pH about 3.5).

To macerate the chloroplasts, the chloroplast fraction was subsequently treated with a hypotonic acid ethanolic solution (pH 3.5) whose ethanol content is preferably in the range of from 30 to 70% by volume, preferably in the range of from 35 to 50% by volume. The result was a yellow solution which was removed from the chloroplast shells obtained as a sediment.

This solution, which is a sort of crude product, can be directly purified by stepwise sterile filtration over filters having pore sizes of 8 μm, 0.45 μm and 0.2 μm, followed by freeze-drying.

However, it is preferred to separate the yellow ethanolic solution via support-free deflection electrophoresis (cf. Kurt Hannig in: Jahrbuch 1968 der Max-Planck-Gesellschaft zur Förderung der Wissenschaften e.V. or Z. Anal. Chem., 181, 244 (1961)), and those fractions which have a yellowish coloration are retained. These fractions are combined.

The fraction which contains the desired protein whose action it is to liberate oxygen from water is preferably concentrated to approximately the 0.3- to 0.7-fold volume of its initial volume by means of an ultrafiltration membrane with a cutting zone in the range from 5000 to 10,000 d, after which the concentrate, which is obtained as the retentate, is dialyzed against acidified pure water so as to remove the buffer (pH about 3.5). The product which has been purified by dialysis is subsequently subjected to a sterile filtration step as described above, and freeze-dried.

However, it is preferred to remove any endotoxins which may be present in the solution before freeze-drying by means of adsorption using suitable adsorbents. Examples of suitable adsorbents are Q-Sepharose, polymyxin B-Sepharose and active carbon. From amongst these adsorbents, active carbon is less preferred since considerable losses of the desired protein material can be observed when it is used.

To prepare an injectable solution, the freeze-dried product is taken up in a physiological saline solution, namely in amounts of about 1 to 28 mg/ml of physiological saline solution. However, it must be pointed out that it has emerged that the desired protein is also contained in an alcoholic solution obtained by direct treatment of comminuted dried leaves and stalks of *Equisetum arvense* with a hypotonic ethanol solution. Such a solution can also be purified in the above-described sense, and subjected to sterile filtration and freeze-drying. Since a hypotonic acid alcohol solution is used as the extraction medium, there is generally no danger of microbiological contamination of the extract obtained.

The protein fraction obtained from *Equisetum arvense* is resolved by SDS gradient gel electrophoresis (PAA 4/30 gel manufactured by Pharmacia Fine Chemicals AB; the samples were prepared and the electrophoresis was carried out as described by the manufacturer) in the presence of a marker. A main band of molecular weight 67000±10000 d was obtained. Weaker secondary bands showed at molecular weights of 83500±10000 and 47000 35 10000. The isoelectric points which were determined by isoelectric focusing were at 4.1 (main fraction; two closely adjacent bands), and also 4.7±0.3 and 5.0±0.3 (weaker bands). A marker was used for the pH range of 4.7 to 10.6.

At higher concentrations, the protein solution has a yellow color, and it decomposes in the presence of proton acceptors or under neutral to slightly basic conditions under exposure to light and heating or under light which contains IR components, liberating oxygen from water while the pH simultaneously drops. When the protein fraction is obtained, care should therefore be taken to maintain acid pH values. It has furthermore proved advantageous to carry out all the steps in connection with the isolation of the protein fraction at low temperatures, advantageously at +4° C. When the buffer has been removed by dialysis against deionized water, a solution is obtained which is unstable under the influence of light, but which can be freeze-dried without problems if light is excluded (colored containers).

II. Obtaining an injectable extract (protein mixture) from embryonic tissue or maternal uterus tissue.

Amniotic sacks of calves or sheep were obtained from an abattoir and opened in a laminar flow cabinet under sterile conditions, and the recovered placentae and umbilical cords and, optionally, embryos and fetuses were immediately shock-frozen to below −20° C., in particular −26° C.

Instead, it is also possible to use maternal uterus tissue of pregnant animals, for example of pregnant sheep and cattle, as the starting material, which is processed analogously.

400 to 500 g of these shock-frozen samples of embryonic tissue are placed in a mixer, 1 liter of weakly acidic to weakly alkaline aqueous ethanol (35% by volume) are added, and the mixture is homogenized in the presence of an extraction agent, the temperature being kept at +4° C. To improve the sedimentation properties or separation properties of sediment components, the homogenisate obtained is shaken for some days in the presence of glass beads, preferably at +4° C., after which the components which are capable of separation are separated off by centrifugation or filtration under sterile conditions.

The resulting filtrate or the supernatant is subsequently subjected to a preferably multi-step sterile filtration (filter pore sizes 8 μm; 0.45 μm; 0.2 μm), the temperature of the solutions always being maintained at +4° C. The filtrate of the last filtration is subsequently freeze-dried.

It is preferred to preventively remove endotoxins by means of adsorption before the freeze-drying step, as in the case of the protein fraction described under I.

An injectable solution can be prepared from the freeze-dried product by taking it up in an aqueous medium (about 1 to 28 mg/ml of aqueous medium or physiological saline solution) under isotonic conditions.

SDS polyacrylamide gel electrophoresis (PAA 4/30 manufactured by Pharmacia Fine Chemicals AB; resolution as described by the manufacturers) gave a main band at 62000±10000 d. Secondary bands showed at 43000±10000 and 13800±5000. Isoelectric focusing gave mixture components having isoelectric points at 4.7±0.3 (main band) and secondary bands at 4.1 (two closely adjacent bands) and 4.8 to 5.1 (three adjacent bands).

In the case of cellulose acetate foil electrophoresis, the extract obtained from placenta and umbilical cord was in the range of the albumin fraction and of the α-globulin fraction (70% albumin; 27.6% $α_1$-globulin; 2.4% $α_2$-globulin).

To obtain the extract from embryonic tissue (placenta/umbilical cords/fetuses), an embryonic tissue of any desired degree of matureness can be used.

III. In-vivo tests on rats.

Fibrosarcomas were produced in Wistar rats by a single subcutaneous administration of 20 mg of 20-methylcholanthrene. As soon as these sarcomas had grown to a size which seemed suitable for the intended experiments, the treatment with the protein fraction obtained from *Equisetum arvense* (abbreviated to MDA) and the embryonic tissue extract acting as a proteinase inhibitor (abbreviated to PI) was started. Both substances were injected subcutaneously or intratumorally in a mixture or immediately one after the other. The effect of this treatment was monitored continuously by monitoring the amount of the urine excreted by the rat (ml/24 h) and the amount of uric acid excreted (mg/24 h), while the amount of feed remained the same and liquid could be taken up ad libitum. The amount of uric acid excreted is taken as a direct measure for the destruction of the tumor cells, since there is only one biochemical catabolic route for the purine bases adenine and guanine from DNA, which route has uric acid as the end product, which is then excreted in the urine. The amount of uric acid excreted per day is hence a measure for the amount of adenine and guanine which has been catabolized, and, since these can only be derived from the DNA of destroyed cells, also a measure for the destruction of DNA in tumor cells and hence of all the tumor cells.

When the tests were concluded, the test animals which had been killed were subjected to a microscopic tissue examination (tumor tissue, tissue of the internal organs).

In the case of a first rat this tumor had an external diameter of 0.8 cm at the beginning of the treatment, the daily subcutaneous injection of 100 mg of MDA in conjunction with a weekly injection of 12 mg of PI resulted in the disappearance of the chemically induced subcutaneous fibrosarcoma. During the treatment it was observed that the daily excretion of uric acid was clearly above the normal range. A normal value of the daily excretion of uric acid was determined in the order of magnitude of 0.4 to 0.6 mg/24 h in the case of healthy animals, and slightly increased values in the range of 0.5 to 1.5 mg/24 h in the case of animals with tumors (in each case constant amount of feed, liquid intake ad libitum).

After the above-described successful preliminary experiment, a further rat having a chemically induced fibrosarcoma (external tumor diameter at the beginning of the treatment about 3×3.5 cm) was treated with increasing doses of DMA and PI which were in each case administered together and injected subcutaneously and intratumorally, following the injection diagram which can be seen from FIG. 1. As a consequence of the intratumoral injections, the daily excretion of uric acid rose to values of 5 and 6.12 mg/24 h, i.e. to the 10-fold of the normal daily excretion amount of 0.4 to 0.6 mg/24 h in the case of healthy rats. FIG. 1 shows the curve of uric acid excretion as a function of the MDA/PI doses administered during the treatment period of 22 days.

After 22 treatment days, the rat was killed, and the post-mortem revealed that, in the region of the left hip, there was a tumor the size of about 5×4×4 cm which extended to the hipbone. The surface where the tumor was cut into was macroscopically dissolved in an area of 3×2×2 cm and was grayish-white in color, with embedded cysts. A thorough microscopic investigation of this tumor area revealed that the tumor tissue changed into edematous loose tissue and necroses, substantial tissue necroses being observed in particular around the cyst-type structures. The external, enclosing tumor tissue consisted of spindle-shaped cells and cell nuclei as well as interspersed, highly polymorphic structures with giant nuclei and chromatin compactions.

The heart, lungs, liver and testes of the rat did not show any abnormalities apart from a venous hyperemia caused by the increased liquid uptake and beginning renal failure.

Figure 2:
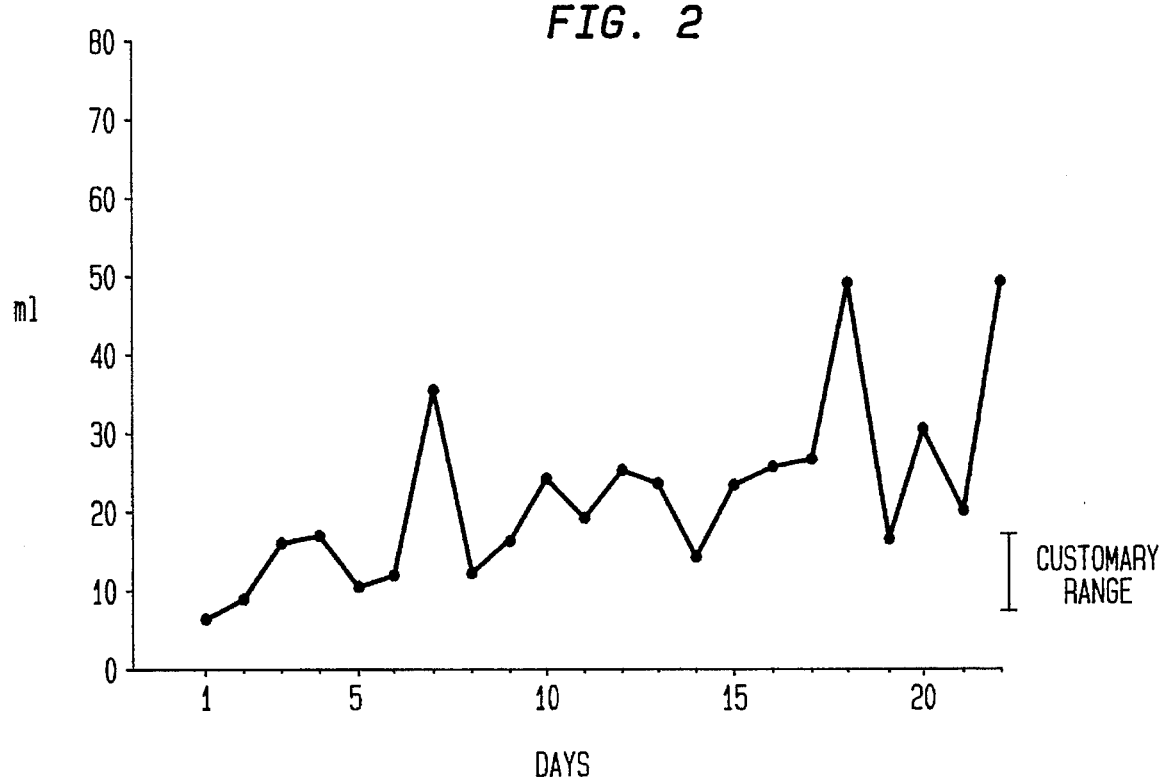
FIG. 2 shows uric acid excretion from a rat treated as in Example III.

FIG. 2 shows a diagram of the daily urine excretion as a function of the MDA/PI doses administered (same rat as in FIG. 1).

Histological findings and the increased excretion of uric acid in the urine demonstrate the destruction of a large amount of tumor cells of the fibrosarcoma.

IV. Medical history

A 66-year-old woman was referred to hospital because of a progressive growth of the left mammary gland. The examination revealed that there were two enlarged, hard axillary nodes on the left. On Feb. 4, 1985, the entire left breast together with an elliptic skin region, the main pectoral muscles and the left axillary lymph node were removed. Macroscopically, the tumor was the size of a fist. To close the wound, it was necessary to carry out a skin transplant from the thigh. Histopathology revealed an invasive ductal carcinoma with metastases in the axillary nodes. Two months after the operation, lymph efflux from the breast resulted in an enlargement in the two left supraclavicular lymph nodes, and extensive formation of metastases had taken place.

As a consequence, 50 mg of MDA were administered daily to the patient, accompanied by injections of 24 mg of PI, administered twice weekly over a period of 15 weeks. Within 2 months, the metastases in the supraclavicular fossa disappeared. By March 1989, the patient had shown no signs whatsoever of a relapse, neither in the clinical findings nor on the basis of the results of biochemical analysis.

It has emerged that the dosage of the substances MDA and PI which are to be administered together, as a function of the nature (stage of development) and size of the particular tumor to be controlled, can be varied within wide limits.

The doses of the two substances are in each case in the range of from 1 to 10 mg/kg of body weight. The two substances MDA and PI are administered here in amounts of essentially equal sizes. The physiological effects of the histological findings show tumor dissolution (necrosis with edema), accompanied by hyperemia in the damaged organ. Only destruction of malign cells is effected selectively, without damage to healthy cells being apparent.

Finally, it must also be mentioned that, for practical reasons, the protein fraction obtained from the photosynthetic system of plants is preferably derived from such plants which do not contain any poisonous components, or components which are otherwise physiologically active in any undesired manner, since the presence of such components makes the process for the preparation of the desired protein fraction more difficult because it is necessary that they be removed. It is therefore preferred to use autotrophic plants as raw materials which usually do not come under the medicinal plants. If such plants are used, it may suffice in favorable cases to treat the comminuted plants with a hypotonic aqueous acidic alcohol solution, without the chloroplast isolation step.

Mention must furthermore be made that the resolution of the ethanolic extract by means of support-free deflection electrophoresis which is described in the present application, only describes one of the possible processes, and that other known separation processes (column-chromatographic processes using molecular sieves or pH gradients such as gel filtration or ion-exchange chromatography or, if appropriate, also affinity chromatography or selective extraction processes) likewise seem to be suitable and may even have advantages for industrial preparation on a larger scale.

I claim:
1. In combination:
a protein fraction with oxygen activity and derived from the photosynthetic system of plants, said protein fraction having a molecular weight of approximately 67000 d±10000 d as determined by SDS gradient gel electrophoresis in the presence of a marker for the pH range of 4.7 to 10.6 and being formed by a process comprising the steps of:
isolating chloroplasts from autotrophic plants or autotrophic lower organisms;
washing the isolated chloroplasts;
treating the isolated and washed chloroplasts with a hypotonic ethanol solution to effect their lysis;
removal of formed sediment;
resolution of the alcoholic solution by support-free deflection electrophoresis to obtain a yellowish, oxygen-liberating protein fraction, and optionally subsequent concentration of this fraction by ultra-filtration, dialysis of the ultrafiltration retentate against water and freeze-drying;
with
a protein mixture derived from calf or sheep embryos and fetuses, said protein mixture comprising proteins yielding a main band at 62000 d ±10000 d and secondary bands at 43000 d±10000 d and 13800 d ±5000 d in SDS polyacrylamide gel electrophoresis, and being formed by a process comprising the steps of
comminuting deep-frozen calf or sheep embryos under sterile conditions in the presence of a polar water-containing organic solvent; and
removing components which are capable of separation from the organic solvent by sedimentation or sterile filtration;
fine filtration and microfiltration of the organic solution which has been freed from the components which are capable of separation;
filling the filtrate into containers without further resolution into protein fractions, and optionally freeze-drying, with
all the process steps mentioned being carried out under sterile conditions, for preparing a pharmaceutical composition for simultaneous or sequential administration by injection or infusion to selectively dissolve cancer cells in live organisms of warm-blooded species.

2. The combination of claim 1 wherein the chloroplasts are isolated from *Equisetum arvense*.

3. A pharmaceutical composition, comprising:
a) a protein fraction with oxygen activity and derived from the photosynthetic system of plants, said protein fraction having a molecular weight of approximately 67000 d±10000 d as determined by SDS gradient gel electrophoresis in the presence of a marker for the pH range of 4.7 to 10.6 being formed by a process comprising the steps of:
isolating chloroplasts from autotrophic plants or autotrophic lower organisms;
washing the isolated chloroplasts;
treating the isolated and washed chloroplasts with a hypotonic ethanol solution to effect their lysis;
removal of formed sediment;
resolution of the alcoholic solution by support-free deflection electrophoresis to obtain a yellowish, oxygen-liberating protein fraction, and optionally subsequent concentration of this fraction by ultrafiltration, dialyale of the ultrafiltration retentate against water and freeze-drying; and
b) a protein mixture derived from calf or sheep embryos and fetuses, said protein mixture comprising proteins yielding a main band at 62000 d±10000 d and secondary bands at 43000 d+10000 d and and 13800 d±5000 d in SDS polyacrylamide gel electrophoresis, and being formed by a process comprising the steps of
comminuting deep-frozen calf or sheep embryos or fetuses under sterile conditions in the presence of a polar water-containing organic solvent; and
removing components which are capable of separation from the organic solvent by sedimentation or sterile filtration;
fine filtration and microfiltration of the organic solution which has been freed from the components which are capable of separation;
filling the filtrate into containers without further resolution into protein fractions, and optionally freeze-drying, with all the process steps mentioned being carried out under sterile conditions,
as a combined preparation for simultaneous or sequential administration by injection or infusion in the treatment of cancer cells in live organisms of warm-blooded species.

4. The pharmaceutical composition of claim 3, containing the protein fraction and the protein mixture in freeze-dried form.

5. The pharmaceutical composition of claim 3 wherein all the process steps for forming the protein mixture are carried out in a laminar flow system at temperatures around +4° C.

6. The pharmaceutical composition of claim 3 wherein the protein fraction and the protein mixture are further purified for removal of endotoxins.

7. A process for selective dissolution of cancer cells in live organisms of warm-blooded species, which process comprises administering by injection or infusion to a patient simultaneously or sequentially as a combined pharmaceutical preparation an effective amount of
a) an amount of a protein fraction with oxygen activity and derived from the photosynthetic system of plants, said protein fraction having a molecular weight of approximately 67000 d±10000 d as determined by SDS gradient gel electrophoresis in the presence of a marker for the pH range of 4.7 to 10.6 and being formed by a process comprising the steps of:
isolating chloroplasts from autotrophic plants or autotrophic lower organisms;
washing the isolated chloroplasts;
treating the isolated and washed chloroplasts with a hypotonic ethanol solution to effect their lysis;
removal of formed sediment;
resolution of the alcoholic solution by support-free deflection electrophoresis to obtain a yellowish, oxygen-liberating protein fraction, and optionally subsequent concentration to this fraction by ultrafiltration, dialysis of the ultrafiltration retentate against water and freeze-drying; and
b) an amount of a protein mixture derived from calf or sheep embryos and fetuses, said protein mixture comprising proteins yielding a main band at 62000 d±10000 d and secondary bands at 43000 d±10000 d and and 13800 d±5000 d in SDS polyacrylamide gel electrophoresis, and being formed by a process comprising the steps of
comminuting deep-frozen calf or sheep embryos or fetuses under sterile conditions in the presence of a polar water-containing organic solvent; and
removing components which are capable of separation from the organic solvent by sedimentation or sterile filtration;
fine filtration and microfiltration of the organic solution which has been freed from the components which are capable of separation;
filling the filtrate into containers without further resolution into protein fractions, and optionally freeze-drying, with all the process steps mentioned being carried out under sterile conditions.

8. The process of claim 7, wherein the preparation process steps are carried out in a laminar flow system at temperatures around +4° C.

9. The process of claim 7, further comprising the step of purifying the protein fraction and the protein mixture for removal of endotoxins.

* * * * *